(12) United States Patent
Knapp (10) Patent No.: US 12,114,966 B2
(45) Date of Patent: Oct. 15, 2024

(54) HEARTBEAT DISPLAY AND NOTIFICATION SYSTEM

(71) Applicant: Stacey Knapp, Santa Cruz, CA (US)

(72) Inventor: Stacey Knapp, Santa Cruz, CA (US)

( * ) Notice: Subject to any disclaimer, the term of this patent is extended or adjusted under 35 U.S.C. 154(b) by 115 days.

(21) Appl. No.: 16/914,488

(22) Filed: Jun. 29, 2020

(65) Prior Publication Data
US 2021/0113095 A1  Apr. 22, 2021

Related U.S. Application Data

(63) Continuation-in-part of application No. 16/865,436, filed on May 4, 2020.

(51) Int. Cl.
*A61B 5/024* (2006.01)
*A61B 5/00* (2006.01)

(52) U.S. Cl.
CPC ............ *A61B 5/024* (2013.01); *A61B 5/0006* (2013.01); *A61B 5/7264* (2013.01); *A61B 5/7405* (2013.01); *A61B 5/742* (2013.01); *A61B 5/7455* (2013.01)

(58) Field of Classification Search
CPC ..... A61B 5/024; A61B 5/0006; A61B 5/7264; A61B 5/7405; A61B 5/742; A61B 5/7455
See application file for complete search history.

(56) References Cited

U.S. PATENT DOCUMENTS

| | | | | |
|---|---|---|---|---|
| D895,673 S | * | 9/2020 | Lyons | D14/489 |
| D912,699 S | * | 3/2021 | Fuchs | D14/492 |
| 11,134,882 B1 | * | 10/2021 | Chen | A61B 5/358 |
| 2004/0034284 A1 | * | 2/2004 | Aversano | A61B 5/0006 |
| | | | | 600/300 |
| 2016/0004224 A1 | * | 1/2016 | Pi | G04G 21/025 |
| | | | | 368/10 |
| 2017/0188864 A1 | * | 7/2017 | Drury | A61B 5/02427 |
| 2017/0367599 A1 | * | 12/2017 | Sanyal | G06N 20/00 |
| 2019/0117070 A1 | * | 4/2019 | Muhsin | G16H 40/67 |
| 2019/0358464 A1 | * | 11/2019 | Volosin | A61B 5/024 |
| 2020/0406000 A1 | * | 12/2020 | Shimizu | A63B 71/0686 |
| 2021/0015442 A1 | * | 1/2021 | Barnacka | G16H 40/67 |
| 2021/0020278 A1 | * | 1/2021 | Chahal | A61B 5/0022 |

* cited by examiner

*Primary Examiner* — Catherine M Voorhees
(74) *Attorney, Agent, or Firm* — The Law Office of Herbert T. Patty (57) ABSTRACT

The present invention relates to an improved heartbeat display and notification system. The system includes retrieving a stream of heartbeat data from an external heart monitoring device. The system further includes storing the retrieved stream of heartbeat data and rendering portions of the stored heartbeat data. Furthermore, the system includes displaying the rendered portions of the stored heartbeat data as a heartbeat rendering. The heartbeat display and notification system also includes determining, and when necessary, updating a user's baseline heart rate. Additionally, the system includes storing the user's baseline heart rate, comparing the user's present heart rate to the user's baseline heart rate. The system further includes generating a heartbeat rendering in response to the comparison and issuing a notification when the difference between the user's present heart rate and the user's baseline heart rate is beyond a pre-defined threshold.

20 Claims, 11 Drawing Sheets

| Misser | Show | A Sat | Aexer | Genere | My Ratings | May Cooxy ▽ | Last Played |
|---|---|---|---|---|---|---|---|
| 1 ☑ Cheng Con | 4:23 | Sayyer Fuyyest | Sayyer Fuyyest | Flvvr | ☆☆☆☆☆ | 25 | 1/4/2006 12:21 |
| 2 ☑ Sver ysrng | 4:36 | Lftl outse | Missrt fslso | Olrge | ☆☆☆☆☆ | 12 | 2/4/2006 12:22 |
| 3 ☑ Oursge | 5:23 | A Sat | Aexer | Genere | ☆☆☆☆☆ | 16 | 3/4/2006 12:26 |
| 4 ☑ Simule NW Carrvo | 3:33 | Sayyer Fuyyest | Sayyer Fuyyest | Flvvr | ☆☆☆☆☆ | 10 | 4/4/2006 12:28 |
| 5 ☑ Rovery | 4:23 | Lftl outse | Missrt fslso | Olrge | ☆☆☆☆☆ | 36 | 5/4/2006 12:24 |
| 6 ☑ Ku yu su | 4:83 | A Sat | Aexer | Genere | ☆☆☆☆☆ | 19 | 6/4/2006 12:21 |
| 7 ☑ Cheng Con | 5:23 | Sayyer Fuyyest | Sayyer Fuyyest | Flvvr | ☆☆☆☆☆ | 18 | 7/4/2006 12:26 |
| 8 ☑ Cheng sen | 3:26 | Lftl outse | Missrt fslso | Olrge | ☆☆☆☆☆ | 16 | 8/4/2006 12:27 |
| 9 ☑ Cunng Xion Cper | 5:23 | Sayyer Fuyyest | Aexer | Genere | ☆☆☆☆☆ | 21 | 9/4/2006 12:24 |
| 10 ☑ whav 1 wayert chey ✪ | 5:15 | Kinfly Serrk ✪ | Sayyer Fuyyest | Flvvr | ☆☆☆☆☆ | 25 | 10/4/2006 12:25 |
| 11 ☑ Cheng Con | 5:16 | A Sat | Aexer | Olrge | ☆☆☆☆☆ | 23 | 11/4/2006 12:21 |
| 12 ☑ Sver ysrng | 5:17 | Sayyer Fuyyest | Sayyer Fuyyest | Genere | ☆☆☆☆☆ | 32 | 12/4/2006 12:26 |
| 13 ☑ Oursge | 4:23 | Lftl outse | Missrt fslso | Flvvr | ☆☆☆☆☆ | 36 | 13/4/2006 12:29 |
| 14 ☑ Simule NW Carrvo | 5:26 | A Sat | Aexer | Olrge | ☆☆☆☆☆ | 29 | 14/4/2006 12:21 |
| 15 ☑ Rovery | 5:48 | Sayyer Fuyyest | Sayyer Fuyyest | Genere | ☆☆☆☆☆ | 70 | 15/4/2006 12:22 |
| 16 ☑ Ku yu su | 5:29 | Lftl outse | Missrt fslso | Flvvr | ☆☆☆☆☆ | 17 | 16/4/2006 12:23 |
| 17 ☑ Cheng Con | 5:23 | A Sat | Aexer | Olrge | ☆☆☆☆☆ | 16 | 17/4/2006 12:24 |
| 18 ☑ Cheng sen | 5:52 | Sayyer Fuyyest | Sayyer Fuyyest | Genere | ☆☆☆☆☆ | 15 | 18/4/2006 12:21 |
| 19 ☑ Cunng Xion Cper | 5:23 | Lftl outse | Missrt fslso | Flvvr | ☆☆☆☆☆ | 14 | 19/4/2006 12:25 |
| 20 ☑ Cheng Con | 4:23 | A Sat | Aexer | Olrge | ☆☆☆☆☆ | 12 | 20/4/2006 12:24 |
| 21 ☑ Sver ysrng | 5:26 | Sayyer Fuyyest | Sayyer Fuyyest | Genere | ☆☆☆☆☆ | 13 | 21/4/2006 12:21 |
| 22 ☑ Oursge | 5:20 | Lftl outse | Missrt fslso | Flvvr | ☆☆☆☆☆ | 14 | 22/4/2006 12:28 |
| 23 ☑ Simule NW Carrvo | 5:13 | A Sat | Aexer | Olrge | ☆☆☆☆☆ | 16 | 23/4/2006 12:29 |
| 24 ☑ Rovery | 5:23 | Sayyer Fuyyest | Sayyer Fuyyest | Genere | ☆☆☆☆☆ | 18 | 24/4/2006 12:21 |
| 25 ☑ Ku yu su | 5:21 | Lftl outse | Missrt fslso | Flvvr | ☆☆☆☆☆ | 15 | 25/4/2006 12:26 |

HEARTBEAT DISPLAY AND NOTIFICATION SYSTEM

CROSS REFERENCE TO RELATED APPLICATIONS

This patent application claims the benefit of U.S. Provisional Ser. No. 62/844,021 filed May 6, 2019 under 35 U.S.C. § 119(e) and further claims the benefit of U.S. Non-Provisional Ser. No. 16/865,436 filed May 4, 2020 under 35 U.S.C. § 120 which is incorporated by reference herein.

FIELD

The present invention relates to an improved heartbeat display and notification system.

BACKGROUND

Trauma is defined as an overwhelming event that causes a perceived or real loss of safety by an individual. If adverse experiences occur during one's childhood, there is a higher risk that one's neurobiology will be impacted. This is especially true if a traumatic event occurs within one's first few years. The impact from these events may not be associated with distinct memories, but rather from a subconscious reaction to perceived threats that manifest in "fight or flight" symptoms. Indeed, this physiology of trauma may be imperceptible to a victim, or may be perceived as normal, and therefore difficult to recognize, diagnose, and treat. The higher the number of Adverse Childhood Experiences (ACEs), the greater the likelihood that emotional dysregulation will have a lifelong impact on an individual. According to the National Center for Disease Control (n.d), "almost two-thirds of adults surveyed reported at least one Adverse Childhood Experience (ACE)—and the majority of respondents that reported at least one ACE reported more than once."

BRIEF DESCRIPTION OF THE DRAWINGS

To facilitate understanding, identical reference numerals have been used, wherever possible, to designate identical elements that are common to the figures. The drawings are not to scale and the relative dimensions of various elements in the drawings are depicted schematically and not necessarily to scale. The techniques of the present invention may readily be understood by considering the following detailed description in conjunction with the accompanying drawings, in which:

FIG. 5 is an exemplary streaming platform with audio and video files.

DETAILED DESCRIPTION

Before the present invention is described in detail, it is to be understood that, unless otherwise indicated, this invention is not limited to specific procedures or articles, whether described or not.

It is further to be understood that the terminology used herein is for the purpose of describing particular embodiments only and is not intended to limit the scope of the present invention.

It must be noted that as used herein and in the claims, the singular forms "a," and "the" include plural referents unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. The term "about" generally refers to ±10% of a stated value.

An improved heartbeat display and notification system and method is disclosed herein. The system includes receiving a stream of heartbeat data from an external heart monitoring device. The streamed heartbeat data is stored via a cloud service or locally in memory on a computing device. Portions of the stored streamed data may be rendered by a software application and displayed by the computing device.

Figure 1:
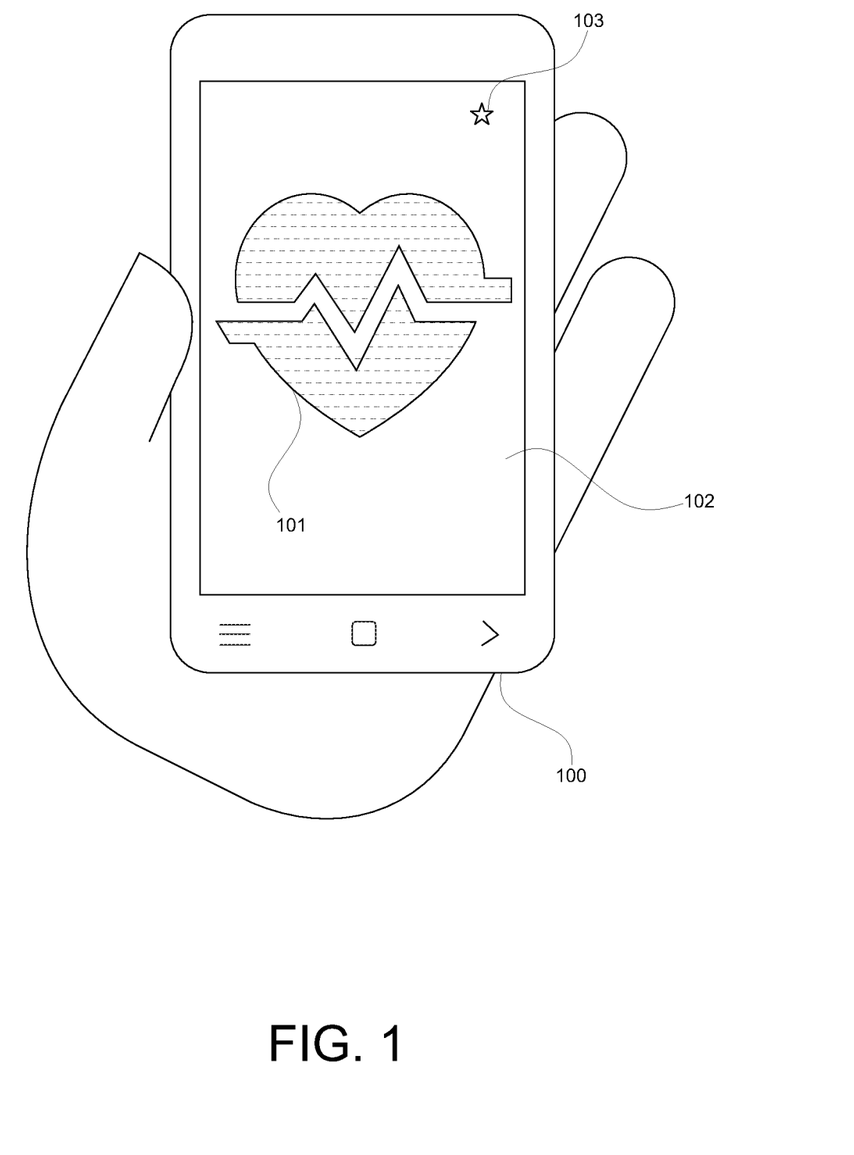
FIG. 1 is an illustration of a smart phone device which displays a heartbeat rendering within a display window of a software application.

FIG. 1 is an illustration of a smart phone device 100 displaying a heartbeat rendering 101 within a display window 102 of a software application 103. The software application 103 (represented by asterisk 103) can process heartbeat data received or retrieved from an external source (as discussed in more detail below) and can present the heartbeat data in various manners. The heartbeat rendering 101 is one implementation in which the heartbeat data is presented to a user within the window 102 of the software application 103. The software application 103 may be equipped with a timer, for use while employing self-regulation strategy activities (e.g., guided meditation). In some implementations, the self-regulation strategy activities include movement-based regulation strategy activities and postural-restoration breathing strategy activities. The self-regulation strategy activities may be embodied as audio, video, or other media file types which aid a user to achieve their baseline heart rate.

Although heart rendering 101 includes a heart-shaped representation of a user's heart, it should be understood by those having ordinary skill in the art that the present invention is not limited to a heartbeat rendering 101 that is heart-shaped, as shown in FIG. 1.

In some implementations, the software application 103 is configured to receive or retrieve steams of a user's heartbeat data from an external heart rate monitoring device. The streams of heartbeat data may be stored in memory accessible locally by software application 103. For example, the software application 103 may be configured such that, for example, four seconds of heartbeat data is received and then stored in memory. In some implementations, the stored streamed data are in segments of pre-defined time periods. In other implementations, the streams of heartbeat data are stored via a cloud service that can be retrieved by the software application 103. The software application 103 may be further configured to retrieve chunks of the stored heartbeat data, generate heartbeat renderings, and present the heart beat renderings via a display component of a computing device. In some implementations, the portions of the stored streamed data may be rendered in succession. For example, the portions of the stored streamed data are rendered in the order in which the streamed data is stored.

In some embodiments of the present invention, the software application 103 retrieves a pre-defined portion of the stored heartbeat data. For example, the software application 103 may retrieve four seconds of heartbeat data to generate the heartbeat rendering and then display the renderings to the user. In other embodiments, the software application 103 may retrieve a pre-defined quantity of memory associated with the stored heartbeat data. For example, the software application 103 may retrieve 2 MB of stored heartbeat data, at a time, to generate heartbeat renderings for display to a user.

The software application 103 may be equipped with customization tools (e.g., an image palette) such that users can personalize the heartbeat renderings 101. For example, users can use the customization tools to add background, to change color and size settings, etcetera. Moreover, the heartbeat rendering 101 can be exported to or integrated within external, proprietary software applications. In addition, the heartbeat rendering 101 may be employed as a Graphic Interchange Format ("GIF") the or video file. The heartbeat rendering 101 may be any digital representation of the user's beating heart. The rendered portions of the stored streamed data can be stored in memory locally or via a cloud service. Machine learning models may be employed to discover trends in the stored heart renderings 101. Further, the heartbeat rendering 101 can be exported to an external, proprietary social network platform with additional customization tools which may be used to add further enhancements to the heartbeat rendering 101.

In one implementation, the software application 103 may prompt users for a setup process upon an initial engagement of the software application 103. The setup process may prompt the user to create goal settings for the frequency in which the user will practice self-regulation strategy activities (e.g., guided meditation exercises). In response to creating the goal settings, the software application 103 can send intention settings to the user to remind them to practice the self-regulation strategy activities. The intention settings may include, but are not limited to, reminders for scheduled guided meditation exercises. In one implementation, the software application 103 "chimes" when it issues notifications to users.

In addition, when the software application 103 is launched by the user, the user is prompted to perform a quick self-regulation activity (e.g., breathing exercise). This feature may be implemented as a default setting of the software application 103. Upon closing the software application 103, a positive affirmation can be presented to the user, such as an image of a dialogue bubble with positive messaging (e.g., "You did a great job!, Come back soon, "See the beauty inside yourself," "Put your hand on your heart today and say I love you!," etc.) on a display component of the user's computing device.

The present invention is designed to support trauma-informed institutions (trauma-informed units) and feature individual pass code log-in credentials and may accommodate multiple users on a software application which employs the present invention. Multiple users can be accommodated by associating each user with a multi-digit (e.g., 4-digit) Personal Identification Number (PIN). Two user types can be specified—administrator or participant. Administrators can create new users (e.g., participants) and assign each new user a PIN. When a user logs in with their PIN, the users can access only the data associated with their account.

Figure 2:
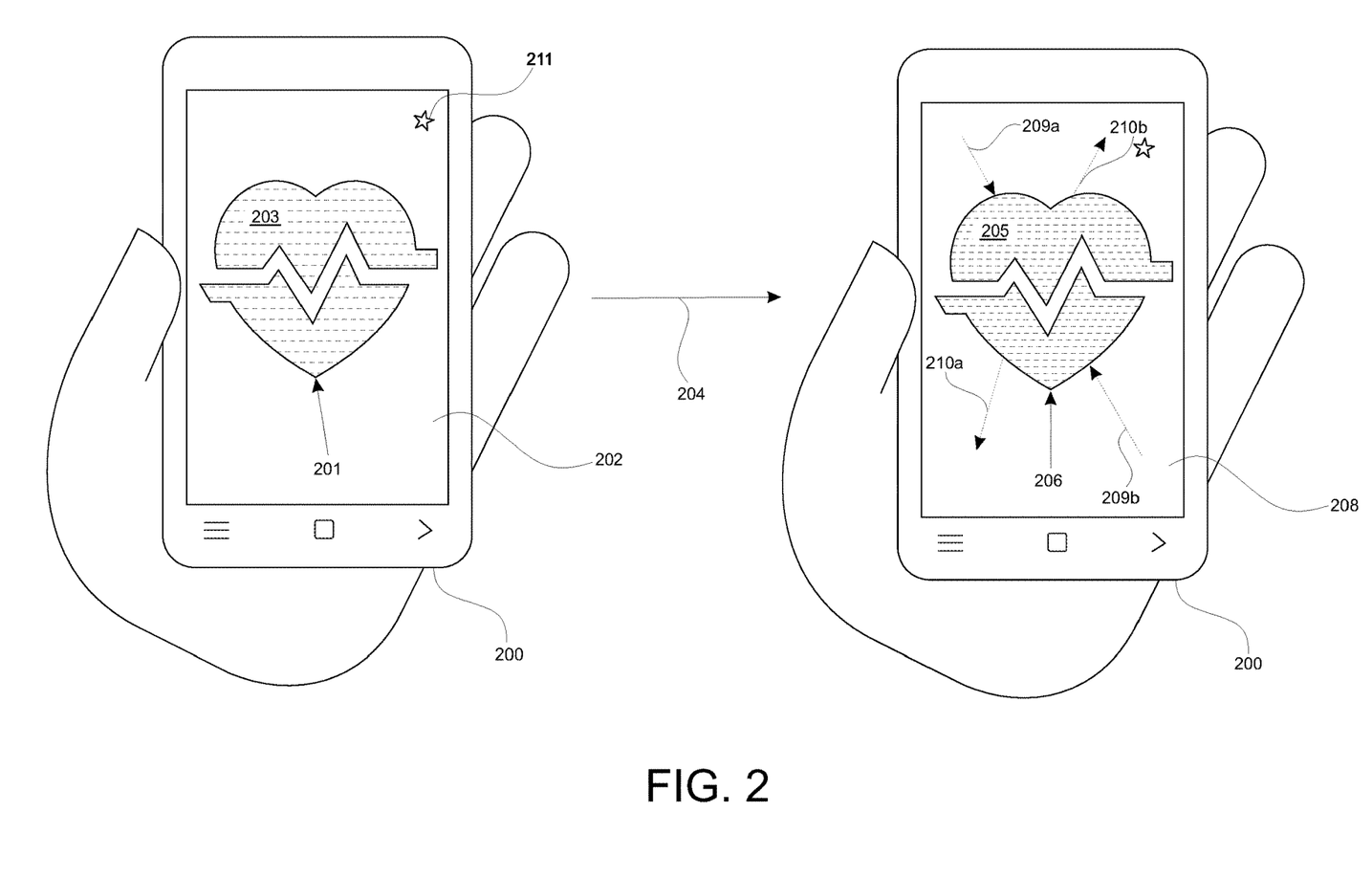
FIG. 2 is an illustration of the heartbeat rendering of FIG. 1 which is capable of changing color and size.

FIG. 2 is an illustration of the heartbeat rendering 201 of FIG. 1 which is capable of changing color and size. As shown, the smart phone device 200 includes a display which displays a heartbeat rendering 201 within a window 202 of a hosted software application 211 (represented by asterisk 211). Notably, the heartbeat rendering 201 may have a first visual effect (e.g., color 203). In some implementations, the color 203 displayed by the heartbeat rendering 201 may be assigned to a baseline heart rate of a user or pre-defined according to a user's heart rate In an event that a user's heart rate changes beyond a pre-defined threshold, the hosted software application 211 may transition (e.g., see arrow 204) to a different color 205 as indicated by heartbeat rendering 206. In some implementations, the pre-defined threshold may be set in a user's default settings. However, a user's settings may be modified and reset based on information the user receives from a medical professional regarding the user's personal vitals (e.g., measured average heart rate).

In some implementations, a vivid blue-green color indicates a baseline resting heart rate whereas heart rates that are higher than a user's baseline heart rate may be indicated by yellow, red, and orange colors. In addition, a user's heart rate which is lower than the user's baseline heart rate can be visualized with a shade of green, blue, and purple. One having ordinary skill in the art should recognize that the aforementioned color schemes are exemplary and therefore the present invention is not limited thereto.

In some implementations, a display device or display component (e.g., such as the display component of the smart phone device 200) may generate several primary colors of light (i.e., red, green, and blue) such that the different colors humans perceive are due to different combinations and intensities of colors.

The changes in color may be a transition in color shade similar to color transitions exhibited by a mood ring. A "mood ring effect" may be characterized by smooth or fluid color transitions which can vary over a surface area of a medium. In some implementations, creating a mood ring effect by a display device may incorporate known artistic techniques such as, but not limited to, simulated texturing, digital-computer micromontage generation, photochromic and thermochromic effects, and pointillism. In addition, creating a mood ring effect for the rendered graphical visualizations (e.g., heartbeat renderings) may cause the variability of color throughout the heartbeat rendering itself. Traditional mood rings may be associated with including cholesteric liquid crystals which have thermochromic material properties. Cholesteric liquid crystals may be capable to change colors in the range of 0.1 to 0.2 seconds.

As such, a software application which employs the present invention may have the capability to change the color of the graphic visualizations in a swift fluid-like manner with forward and reversible capability.

Accordingly, the color changes in the graphic visualization renderings can transition to colors in both a forward and reversible manner along a color spectrum. For example, when a user's heart rate increases, the heartbeat rendering may transition in a forward manner to warmer colors (e.g., orange or red) on the color spectrum. Alternatively, when a user's heart rate decrease, the heartbeat rendering 206 may transition in a reverse manner to cooler colors (e.g., green or blue) on a color spectrum.

Additionally, the heartbeat rendering 206 displayed by the hosted software application 211 can change in size. Minimize arrows 209a, 209b and maximize arrows 210a, 210b of heartbeat rendering 206 are illustrative that the heartbeat rendering 206 can change in size. In some implementations, the change in size of the heartbeat rendering 206 may be in response to a change in the user's heart rate or degree of change from the user's baseline heart rate.

Figure 3:
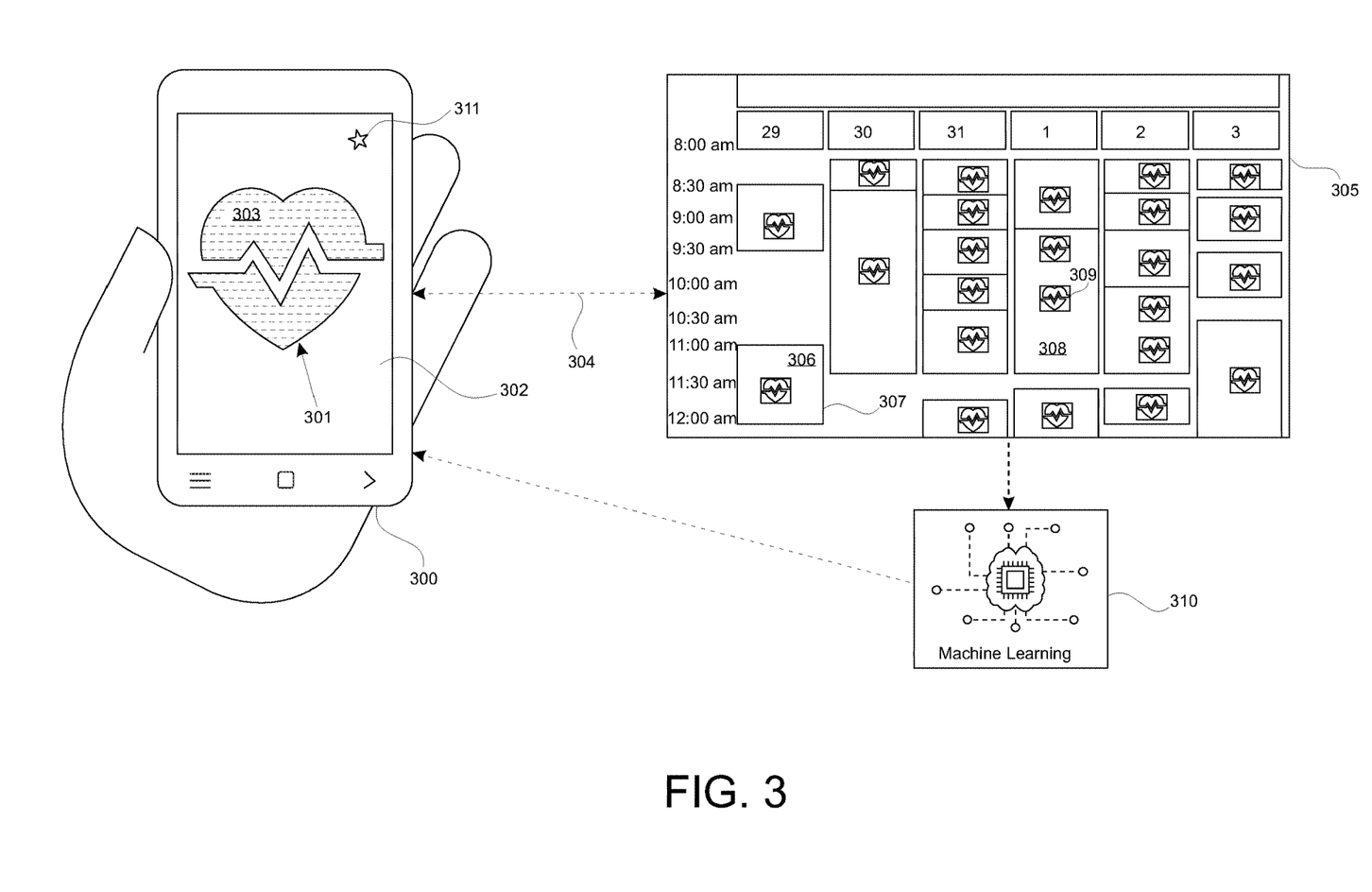
FIG. 3 is an illustration of a smart phone device equipped with a heartbeat display and notification system synced to a calendar system and a machine learning sub-system.

FIG. 3 is an illustration of a smart phone device 300 equipped with a heartbeat display and notification software application 311 (represented by asterisk 311) synced 304 to a calendar system 305 and a machine learning sub-system 310. Notably, the smartphone device 300 hosts software application 311 which can process heartbeat data received from an external device (as will be discussed further) and can present said data in various manners. For instance, the heartbeat rendering 301 is a manner in which the heartbeat data is presented to a user within the window 302. In some implementations, the hosted software application 311 may be further or alternatively equipped with a timer, for use while employing self-regulation strategy activities. The smartphone device 300 displays a heartbeat rendering 301 within a window 302 of the hosted software application 311. Notably, the heartbeat rendering 301 may have a first visual effect (e.g., color 303). In some implementations, the color 303 displayed by the heartbeat rendering 301 may be assigned to a baseline heart rate of a user or pre-defined according to a user's heart rate.

The software application 311 employed by the smart phone device 300 may be linked to a user's calendar system 305. As shown, the calendar system 305 may have several events 306, 308. In one implementation, the graphic visualizations (e.g., heartbeat rendering) may be mapped to a specific event on the calendar system 305 based on a date and timestamp that the user's heart rate was detected. In other implementations, the events pane on the event panes calendar system 305 may be colored in a manner associated with the user's present heart rate or deviation from the user's baseline heart rate. Alternatively, the calendar system 305 may be colored in a manner associated with the user's present heart rate without necessarily being tied to events on the calendar system 305. For example, days, weeks, months, years, etc. on a calendar system 305 may display a background color in accordance with a pre-defined color scheme that is associated with the user's average heart rate during the time period of interest.

Accordingly, the calendar system 305 depicts the user's heart rate in accordance with an average of the user's heart rate, or deviation from the user's baseline heart rate, during specific hours, days, months, years of interest. For example, if the calendar system 305 is configured to depict the color assigned to the user's heart rate per hour, the background color depicted for each hour on the calendar system 305 may reflect the average of the user's heart rate during the hour as received or retrieved from an external heart rate monitor, or alternatively, the average deviation from the user's baseline heart rate during this time period. Likewise, if the calendar system 305 is configured to depict the color associated with the user's heart rate per month, the background color depicted for each month of a calendar year on the calendar system 305 reflects the average of the user's heart rate during the month of interest. Accordingly, the colors displayed by the calendar system 305 can communicate to users its average of their heart rates, and implicitly its stress levels, for certain periods of time.

In addition, the calendar system 305 may also publish intention settings for scheduled self-regulation strategy activities. The activities associated with the intention settings may be color-coded on calendar events according to the user's performance of their goal settings. Accordingly, the color coding of event panes within the calendar system 305 can visually communicate how users adhere to their goals for practicing self-regulation strategy activities.

Figure 4:
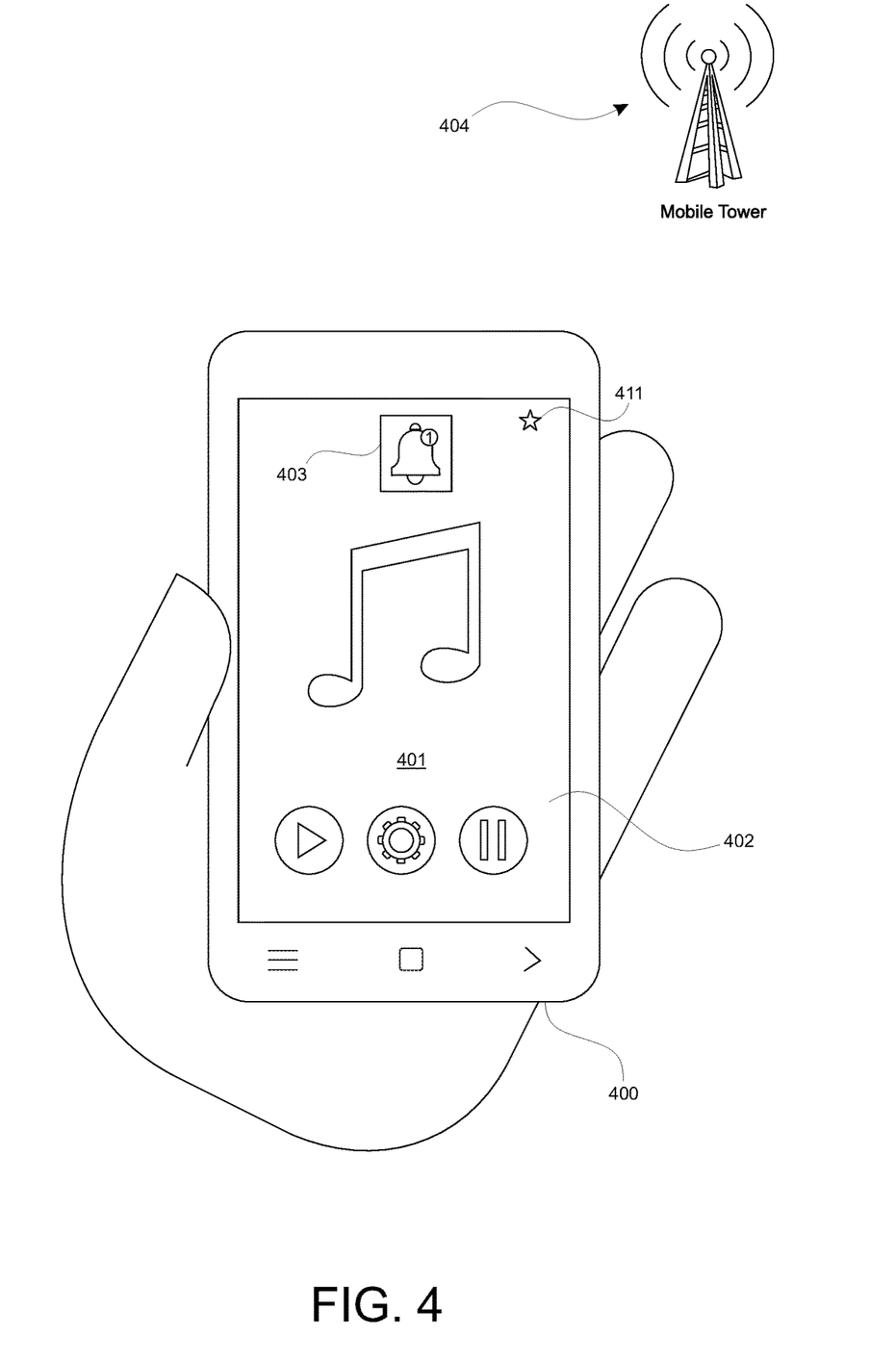
FIG. 4 is an illustration of the smart phone device of FIG. 3 which displays the result of a media player that streams an audio file with guided meditation content.

FIG. 4 is an illustration of the smart phone device 400 of FIG. 3 which includes a display 402 which displays the result of a media player 401 that streams an audio file (not shown) with guided meditation content. The smart phone device 400 may receive information (e.g., streamed media) from a mobile tower 404. Notably, the guided meditation content may be used by users as an exemplary self-regulation strategy activity to get the user's heart rate back to a baseline condition. For example, a timer functionality of the smart phone device 400 or the hosted software application 411 may play a Buddhist bowl chime audio track. In some implementations, while using other features, the heart rendering may recede to an upper corner of a display window within the software application 411.

In some implementations, the software application 411 can display a bell icon 403 which can chime or make any other suitable sound during the commission of the guided mediations. For example, the bell icon 403 may be employed as a notification at the beginning or ending of a guided meditation audio file.

FIG. 5 is an exemplary self-regulation strategy platform 500 with audio and video files. The streaming platform 500 may give a user access to audio, video, or audiovisual files which facilitate guided meditations. The streaming platform 500 may be accessed via a computing device (e.g., smart phone, tablet, desktop computer) which hosts a software application which employs the present invention. In some embodiments, the streaming platform 500, when accessed, prompts the user with specific audio or video media or genre(s) which best facilitate self-regulation.

Notably, users can designate their favorite media files 503 for self-regulation. The user's favorite self-regulation strategy media files 503 may be promoted to the top of the user interface of the streaming platform 500. The self-regulation strategy media files 501 may be further organized by topic 502, frequency, etc. on the streaming platform 500.

Figure 6:
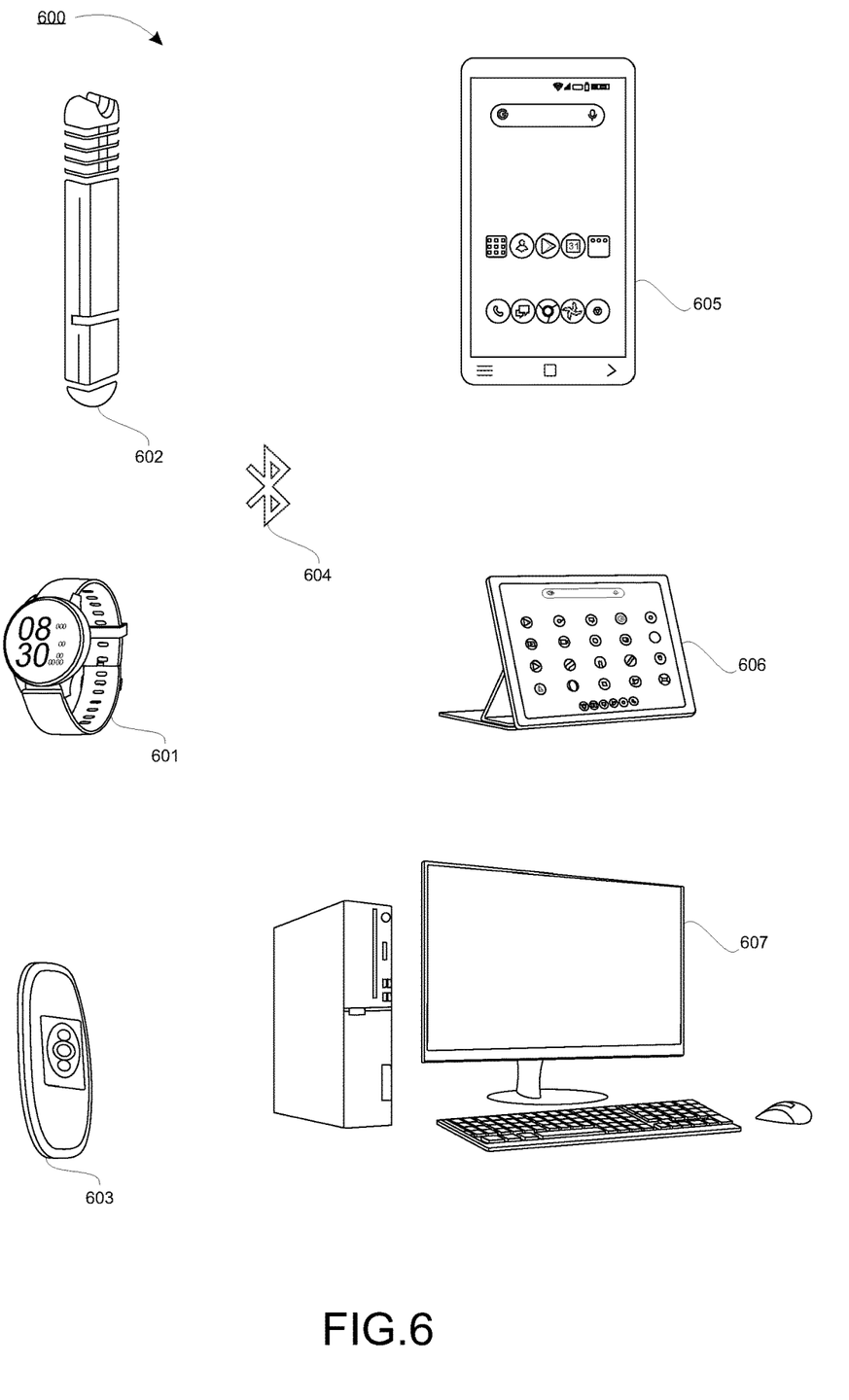
FIG. 6 is a heartbeat display and notification system according to one or more embodiments of the present invention.

FIG. 6 is a heartbeat display and notification system 600 according to one or more embodiments of the present invention. As shown, the heartbeat display and notification system 600 includes an external heart rate monitor device paired (e.g., Bluetooth network 604) to one or more computing devices. Most notably, the heartbeat display and notification system 600 may leverage one or more external, proprietary medical devices. For example, the system 600 may include insertable wearable device 601, cardiac monitors 602, mobile cardiac telemetry devices 603, helter monitors, etc. which can retrieve user heartbeat data In some embodiments, the heartbeat display and notification system 600 may be interoperable with pre-existing or proprietary devices or systems. For instance, the medical devices 602, 603 may be components of a proprietary medical system that can be deployed by medical personnel or medical organizations. Furthermore, a computing device (e.g., smart phone device 605, tablet 606, and desktop computer 607) can be paired to medical devices 602, 603 such that a software application, hosted on a computing device, can receive or retrieve information from the devices 602, 603. Therefore, although the proprietary medical devices 602, 603 can retrieve or generate complex heart rhythm data and related heart condition data, a software application which employs the present invention can receive or retrieve only heartbeat data and then render graphic visualizations that are displayed to users via the software application. Moreover, in some implementations, the heartbeat display and notification system 600 may be configured such that a computing device that hosts the software application that employs the present invention can pair with proprietary medical devices 602, 603 such that heartbeat data can be received or retrieved and then rendered in an efficient manner.

Figure 7:
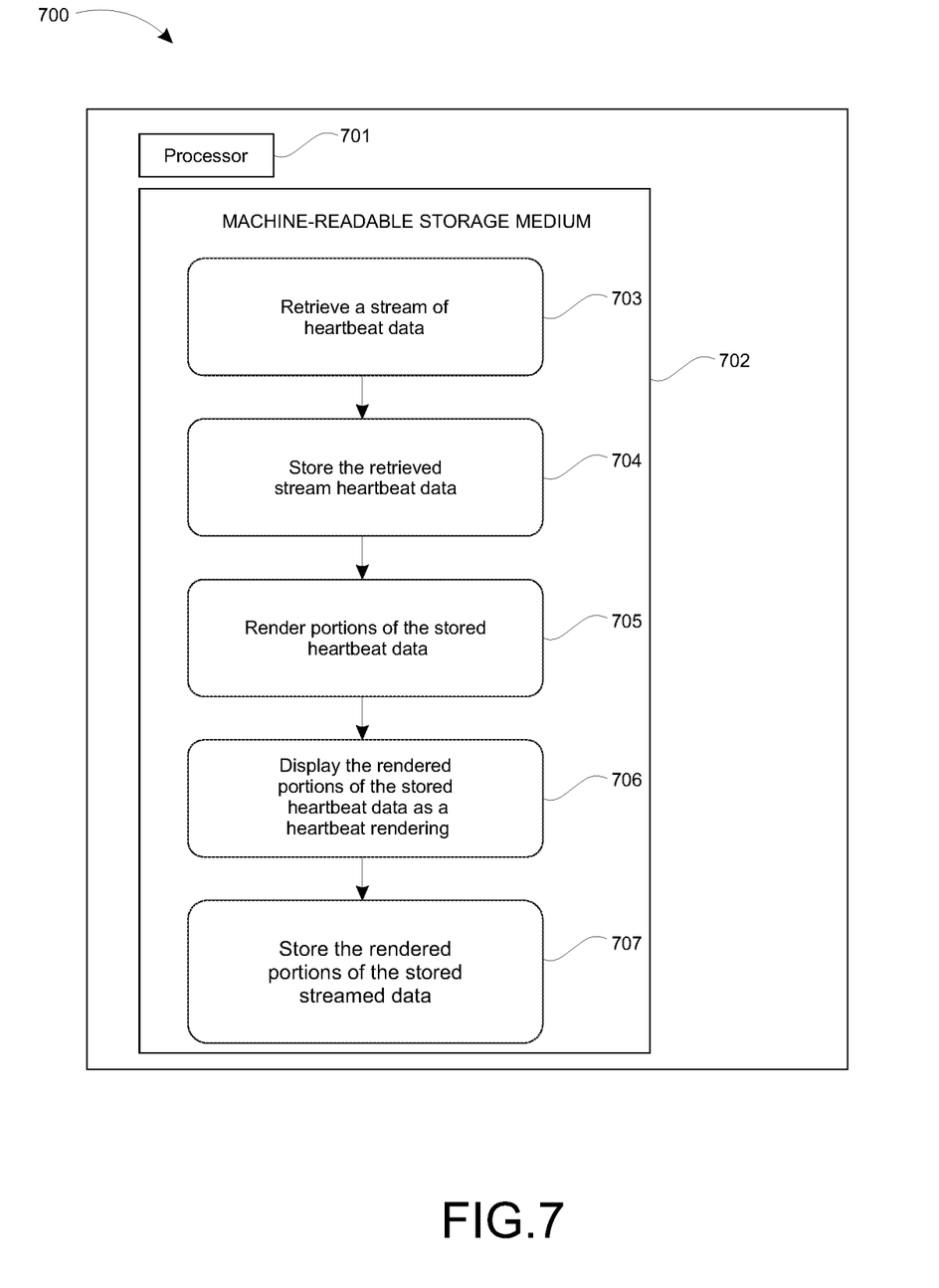
FIG. 7 is an illustration of a computing system according to one or more embodiments of the present invention.

FIG. 7 is an illustration of a computing system 700 according to one or more embodiments of the present invention. The computing system 700 may include a non-transitory computer readable medium 702 that includes computer executable instructions 703-707 stored there on that, when executed by one or more processing units 701 (one processor shown), causes the one or more processing units 701 to effect a heart rendering display process.

Computer executable instructions 703 include instructions to receive a stream of heartbeat data. In some embodiments, the streams of heartbeat data is received from an external heart monitoring device. In addition, computer readable medium 702 includes computer executable instructions 704 to store the streamed heartbeat data in a cloud or locally in memory on a computing device. Next, computer readable medium 702 includes computer executable instructions 705 to render by software application portions of the stored streamed data. Further, computer executable instructions 706 include instructions to display the rendered portions of the stored streamed data as a heartbeat rendering. Finally, computer readable medium 702 includes computer executable instructions 707 to store the rendered portions of the stored streamed data.

Figure 8:
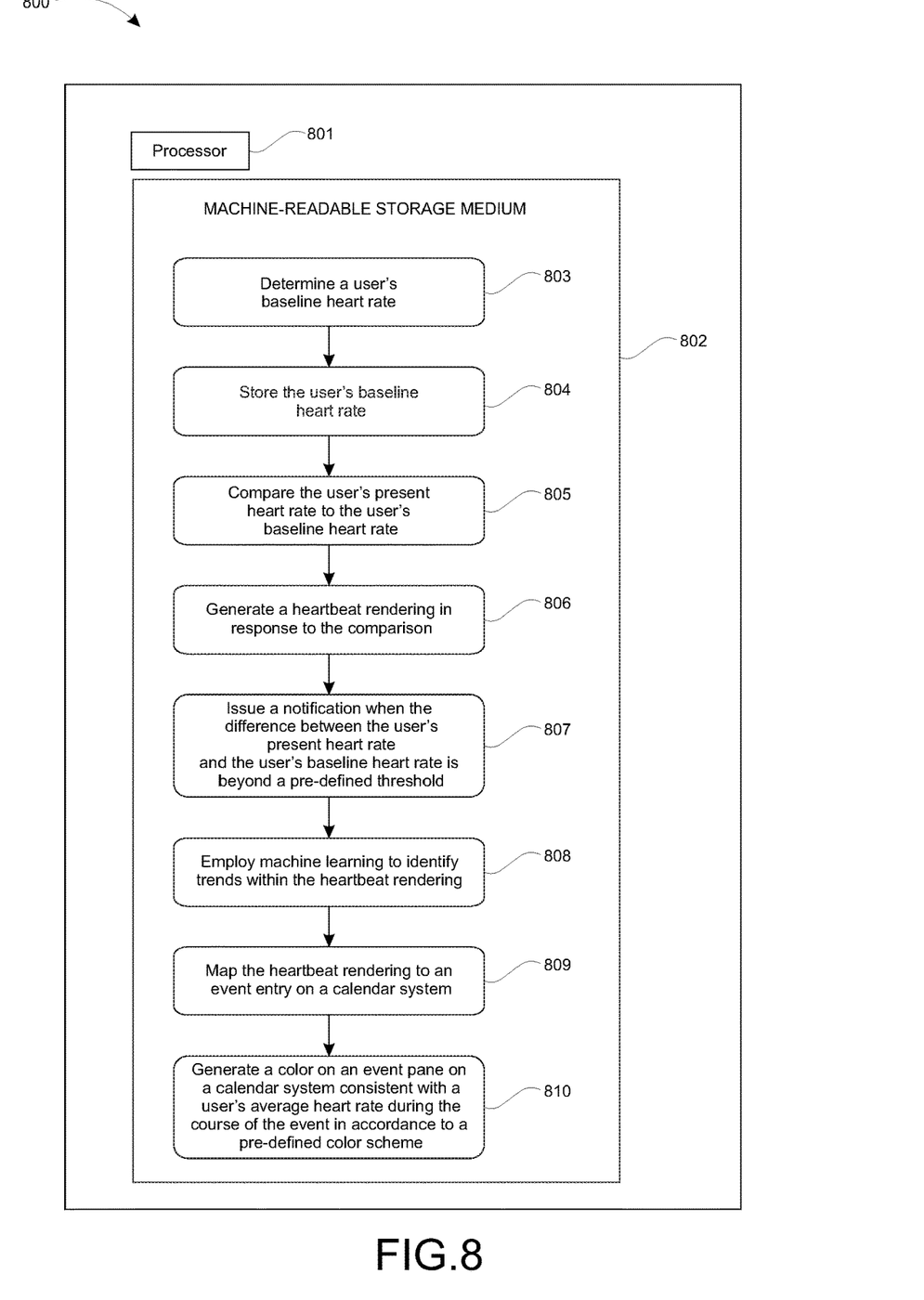
FIG. 8 is an illustration of another computing system according to one or more embodiments of the present invention.

FIG. 8 is an illustration of a computing system 800 according to one or more embodiments of the present invention. The computing system 800 may include a non-transitory computer readable medium 802 that includes computer executable instructions 803-809 stored there on that, when executed by one or more processing units 801 (one processor shown), causes the one or more processing units 801 to effect a heartbeat rendering and display process.

Computer executable instructions 803 include instructions to determine a user's baseline heart rate data and when necessary, updating the user's baseline heart rate. In some implementations, determining the user's baseline heart rate data is accomplished by measuring the user's baseline heart rate data via a heart rate monitor or other suitable device. Further, computer readable medium 802 includes computer executable instructions 804 that include instructions to store the user's baseline heart rate. Furthermore, computer readable medium 802 includes computer executable instructions 805 that include instructions to compare the user's present heart rate to the user's baseline heart rate.

Next, computer executable instructions 806 include instructions to generate a heartbeat rendering in response to the comparison. Further, computer readable medium 802 includes computer executable instructions 807 that include instructions to issue a notification when the difference between the user's present heart rate and the user's baseline heart rate is beyond a pre-defined threshold.

In the present invention, the notifications may be sent to any of a school administrator, medical personnel or directly to a medical center, or any other authorized individual or organization. In some implementations, the notifications are intended to provide accountability to users to implement and/or practice the self-regulation strategy activities. Next, computer executable medium 802 includes computer executable instructions 808 to employ machine learning to identify trends of the user's present heart rate. Furthermore, the computer readable medium 802 includes computer executable instructions 809 to map the heartbeat rendering to an event entry on a calendar system. Lastly, computer executable medium 802 includes computer executable instructions 810 to generate a color on an event pane on a calendar system consistent with a user's average heart rate during the course of the event in accordance to a pre-defined color scheme.

Figure 9:
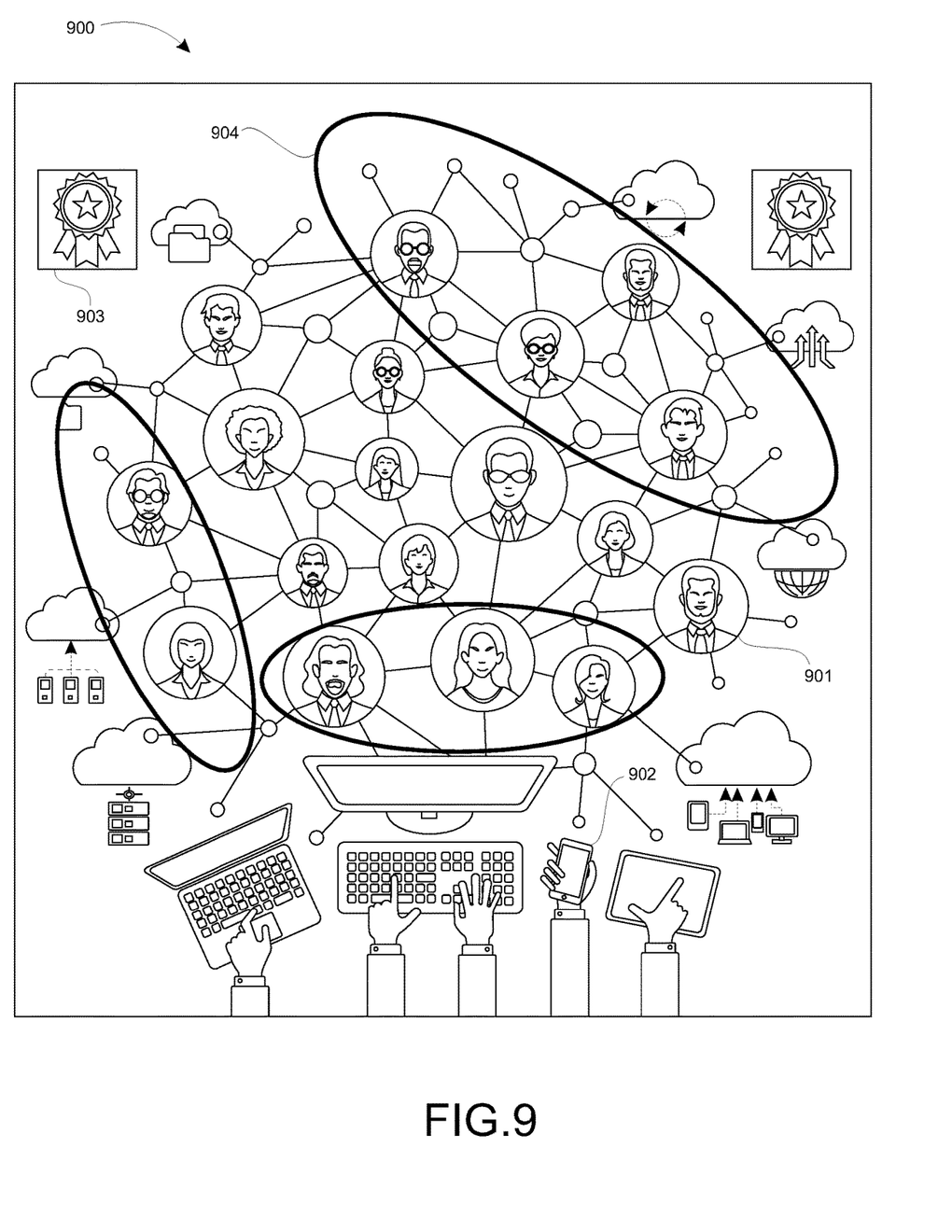
FIG. 9 is an exemplary social network platform which users can track and share listings and performance logs of self-regulation performance activities.

FIG. 9 is an exemplary social network platform 900 which users 901 can track and share listings and performance logs of self-regulation strategy activities. Social network platform 900 has communities of users 904 which provide a mechanism for users to communicate on the platform 900 with any suitable computing device 902. For example, the communities of users 904 include a friends' list. Users can set goals associated with practicing self-regulation strategy activities and can report their self-regulation performance relative to the user's goals. The number of exercises performed by a user may be tallied (and rated) and in response to the user's submissions, the social network platform 900 can issue awards (e.g., badges) to the users. For example, a user 901 may receive any of a badge 903, credit, giveaway, or other incentive as an award.

Figure 10:
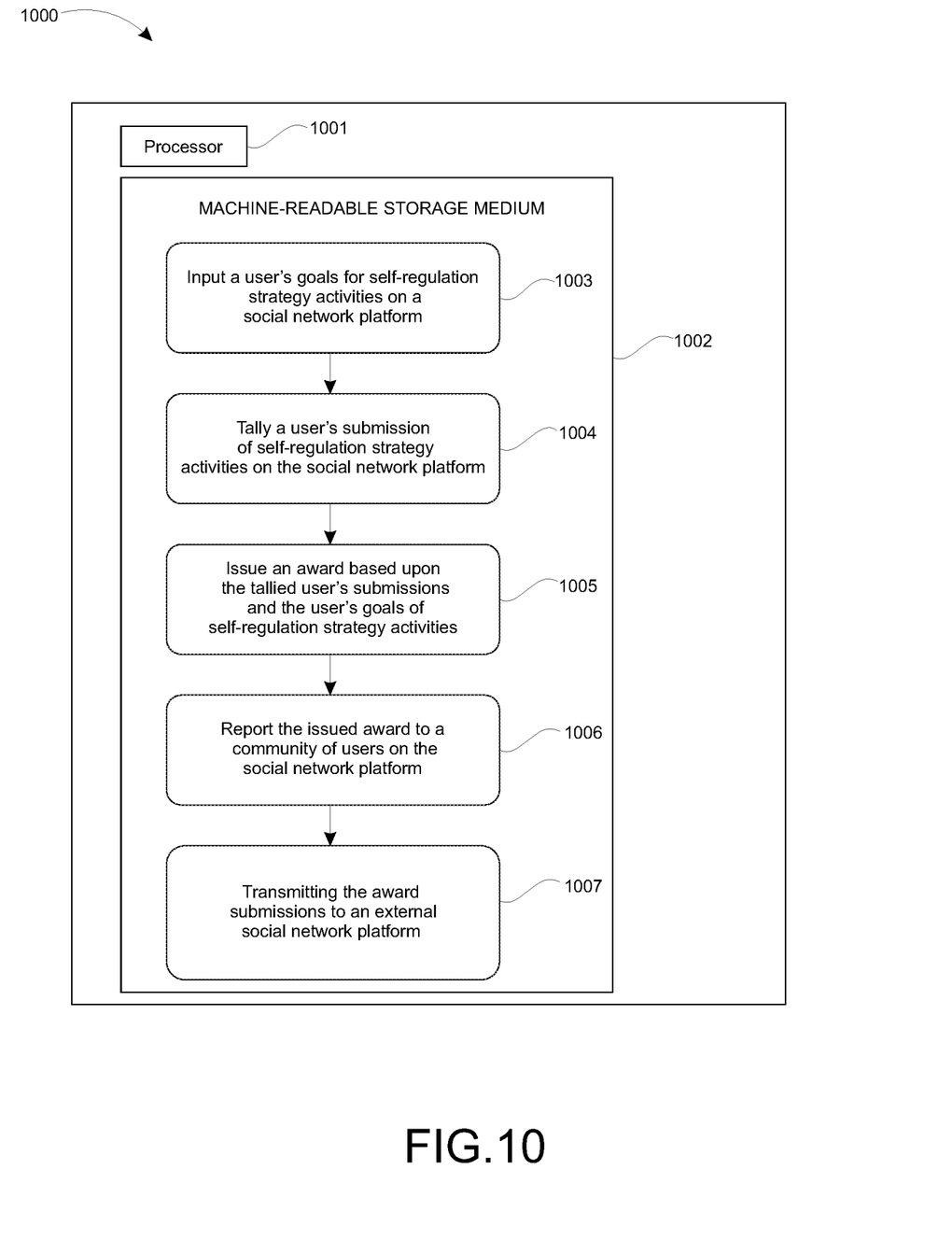
FIG. 10 is yet another illustration of a computing system according to one or more embodiments of the present invention.

FIG. 10 is another illustration of a computing system 1000 according to one or more embodiments of the present invention. The computing system 1000 includes a non-transitory computer readable medium 1002 that includes computer executable instructions 1003-1007 stored there on that, when executed by one or more processing units 1001 (one processor shown), causes the one or more processing units 1001 to effect an activity tallying process.

In some implementations, active users on the social network platform 900 which are presently performing any of the self-regulation strategy activities associated with the user's intention settings may be displayed within a designated window of the software application. For example, a list of usernames or handles associated with users on the social network platform 900 which are performing a self-regulation activity associated with a user's profile may be displayed within the display window. As such, the social network platform 900 can facilitate a supporting environment for users to reach their performance goals.

Computer executable instructions 1003 include instructions to input user's goals for self-regulation strategy activities on a social network platform. Computer readable medium 1002 further includes computer executable instructions 1004 to tally a user's goals for self-regulation strategy activities on the social network platform. In addition, computer executable instructions 1005 include instructions to issue an award based on the tallied self-regulation strategy activities. Next, computer readable medium 1002 includes computer executable instructions 1006 which include instructions to report the issued awards to a community of users on the social network platform. Lastly, computer readable medium 1002 includes computer executable instructions 1007 to transmit the award submissions to an external, proprietary social network platform.

Figure 11:
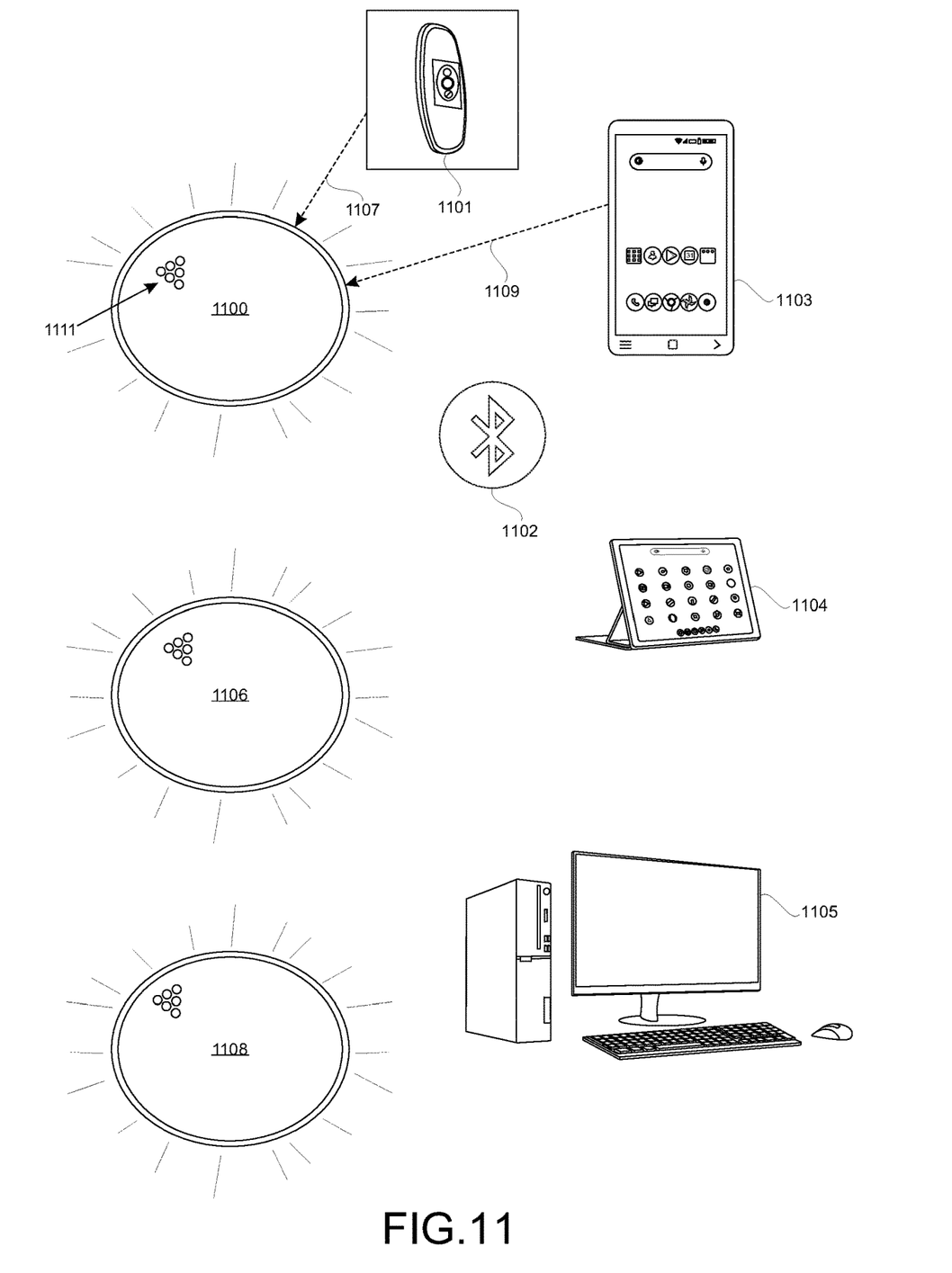
FIG. 11 is an illustration of an apparatus which can project a rendering of a user's heart rate signature according to one or more embodiments of the present invention.

FIG. 11 is an illustration of a system of orb device 1100 which can project a rendering of a user's heart beats. In particular, FIG. 11 shows an orb device 1100 which has a dual function to both render a user's heartbeats and to serve as a paper weight. A user has the option to obtain a graphical visualization (e.g., rendering) of the user's heartbeats via one or more exemplary computing devices 1103, 1104, or 1105. In one implementation, the orb device 1100 may be communicatively coupled over a network 1102 (e.g., Bluetooth) to one or more of the computing devices 1103, 1104, 1105 assigned to a user. For example, the orb device 1100 may be paired with a user's smart phone device 1103.

In some embodiments, the orb device 1100 renders a user's heartbeats via emanating lights 1100 lodged within or upon an external surface of the orb device 1100. The lighting may vary in intensity, color, or location. In addition, the orb device 1100 may also employ haptics to help create heart rendering effects. The exemplary computing devices 1103, 1104, 1105 can be used to program the orb device 1100 with regards to its lighting effects. In addition, the orb device 1100 may include speakers 1111 which can output audible effects in response to changes or a state of a user's heart rate. Moreover, the orb devices 1100, 1106, 1108 can output from its speakers audio from the guided meditation audio files (e.g., Buddhist chime).

The present invention may also facilitate a system of orb devices 1100 assigned to a unique user. For example, a user may have three orb devices 1100, 1106, 1108 which output their personal heart rate signature (e.g., orb device 1100) and those of two loved ones (e.g., spouse and child—or devices 1106, 1108). In this example, both the user's spouse and child have provided consent for the user to access its personal heart rate data. Accordingly, a user can expeditiously react (e.g., contact with its spouse, or seek medical help, etc.) to changes to their loved one(s) heart rate based upon the visual (e.g., lighting), haptic or audible effects emanated from orb device 1106 (e.g., assigned to the user's spouse) or from orb device 1108 (e.g., assigned to the user's child).

Each of the orb devices 1100, 1106, 1108 may contain one or more processors, wireless circuitry, power circuitry, and other necessary electronics to process instructions (e.g., commands) and communication with each other, the one or more coupling devices 1103, 1104, 1105, or external medical devices (e.g., heart rate monitor). For example, the orb devices 1100, 1106, 1108 may communicate with smartphone device 1103 (arrow 1109) with a software application which employs the present invention hosted thereon to retrieve the user's baseline heart rate and may communicate with an external heart rate monitor 1101 to receive the user's present heart rate (arrow 1107).

In addition, the orb devices 1100, 1106, 1108 can output personalized audible messages. For example, if a user's heart rate exceeds the user's baseline heart rate, the orb device 1106 which is assigned to the user's spouse can output a personalized audible message to encourage the user to engage in one or more self-regulation strategy activities. Accordingly, users which have been assigned an orb device may create personalized messages to other users in their network.

In some implementations, each orb device effects a unique lighting color scheme according to the user's that the user settings. However, it should be understood by those having ordinary skill in the art that a software application which employs the present invention can be configured to transform each color scheme to be consistent with the color scheme attributed to the user settings which has possession of the orb devices 1100, 1106, 1108. Accordingly, a user in possession of the orb devices 1100, 1106, 1108 can easily ascertain the heartbeat/heart rate states of the users which the orb devices 1106, 1108 are assigned to.

The heartbeat display and notification system can be used by educators, educational staff, students, parents or anyone seeking to decrease the physiological symptoms associated with stress and better understand the impacts of stress and the benefits of mindfulness practices. Educators can also benefit from the practice of self-care and mindfulness strategies and will be encouraged to model these strategies in classrooms. Students working with one-on-one mentors, behavioral staff or school nurses can benefit from the repetitive practices offered in intervention settings of using the device to measure and compare heart rates before and after implementing self-regulation strategy practice.

While illustrative implementations of the application have been described in detail herein, it is to be understood that the inventive concepts may be otherwise variously embodied and employed, and that the appended claims are intended to be construed to include such variations, except as limited by the prior art.

Reference throughout this specification to "one implementation" or "an implementation" means that a particular feature, structure, or characteristic described in connection with the implementation is included in at least one implementation of the present invention. Thus, the appearances of the phrases "in one implementation" or "in some implementations" in various places throughout this specification are not necessarily all referring to the same implementation. Furthermore, the particular features, structures, or characteristics may be combined in any suitable manner in one or more implementations.

Systems and methods describing the present invention have been described. It should be understood that the descriptions of some embodiments of the present invention do not limit the various alternative, modified, and equivalent embodiments which may be included within the spirit and scope of the present invention as defined by the appended claims. Furthermore, in the detailed description above, numerous specific details are set forth to provide an understanding of various embodiments of the present invention. However, some embodiments of the present invention may be practiced without these specific details. In other instances, well known methods, procedures, and components have not been described in detail so as not to unnecessarily obscure aspects of the present embodiments.

What is claimed is:

1. A non-transitory machine-readable storage medium containing instructions that, when executed, causes a smart phone device to:

determine a user's baseline heart rate;

store the user's baseline heart rate;

compare the user's present heart rate to the user's baseline heart rate;

generate heartbeat rendering instructions in response to the comparison; and send the generated heartbeat rendering instructions to a first orb device that is communicatively coupled to the smart phone device to display the user's heartbeat rendering;

wherein the generated heartbeat rendering instructions include instructions to vary light in color and intensity within the first orb device;

wherein when the user's heart rate is at the user's baseline heart rate, the heart rate rendering is a first color and first intensity and upon detecting a change from the user's baseline heart rate, the heart rate rendering changes from the first color and first intensity to a second color and a second intensity to reflect the change in the user's heart rate.

2. The non-transitory machine-readable storage medium of claim 1, further comprising instructions that, when executed, causes the smart phone device to update the user's baseline heart rate.

3. The non-transitory machine-readable storage medium of claim 1, wherein the user's baseline heart rate is an average heart rate data during a pre-defined time period.

4. The non-transitory machine-readable storage medium of claim 1, wherein the user's present heart rate is continuously retrieved by the smart phone device from an external heart rate monitor.

5. The non-transitory machine-readable storage medium of claim 1 further comprising issuing a notification in a form of at least one of an audible tone, visual indicia, haptic effect, or audiovisual indicia when a difference between the user's present heart rate and the user's baseline heartrate is beyond a pre-defined threshold based on a first set of preferences.

6. The non-transitory machine-readable storage medium of claim 1, further comprising instructions that, when executed, causes the smart phone device to employ machine learning to identify trends within the heartbeat rendering.

7. The non-transitory machine-readable storage medium of claim 1, further comprising instructions that, when executed, causes the smart phone device to map the heartbeat rendering to an event entry on a calendar system.

8. The non-transitory machine-readable storage medium of claim 7, wherein the calendar system includes heartbeat renderings associated with several users.

9. The non-transitory machine-readable storage medium of claim 8, further comprising instructions that, when executed, causes the smart phone device to generate a color on an event pane on a calendar system indicative of a user's average heart rate during the course of the event in accordance to a pre-defined color scheme.

10. The non-transitory machine-readable storage medium of claim 1 further comprising instructions that, when executed, causes the smart phone device to generate heartbeat rendering instructions that varies light within a location within the first orb device.

11. The non-transitory machine-readable storage medium of claim 1 further comprising instructions that, when executed, causes the smart phone device to send the generated heartbeat rendering instructions to a second orb device that is communicatively coupled to the smart phone device to display the user's heartbeat rendering.

12. The non-transitory machine-readable storage medium of claim 11, wherein the first orb device and the second orb device are communicatively coupled to each other.

13. The non-transitory machine-readable storage medium of claim 1 further comprising instructions that, when executed, causes the smart phone device to generate instructions to send instructions to the second orb device to output personalized audible messages.

14. The non-transitory machine-readable storage medium of claim 1 further comprising instructions that, when executed, causes the smart phone device to assign a first unique lighting color scheme to the first orb device and a second unique lighting color scheme to the second orb device.

15. A non-transitory machine-readable storage medium containing instructions that, when executed, causes a smart phone device to:

determine a user's baseline heart rate;

store the user's baseline heart rate;

compare the user's present heart rate to the user's baseline heart rate;

generate a first set of heartbeat rendering instructions in response to the comparison; and send the first set of generated heartbeat rendering instructions to a first orb device that is communicatively coupled to the smart phone device to display the user's heartbeat rendering;

wherein the first set of generated heartbeat rendering instructions include instructions to vary light in color and intensity within the first orb device;

wherein when the user's heart rate is at the user's baseline heart rate, the heart rate rendering is a first color and first intensity and upon detecting a change from the user's baseline heart rate, the heart rate rendering changes from the first color and first intensity to a second color and a second intensity to reflect the change in the user's heart rate generate a second set of heartbeat rendering instructions in response to the comparison; and send the second set of generated heartbeat rendering instructions to a third orb device that is communicatively coupled to the smart phone device to display the user's heartbeat rendering;

wherein the second set of generated heartbeat rendering instructions include instructions to vary light in color and intensity within the third orb device;

wherein when the user's heart rate is at the user's baseline heart rate, the heart rate rendering is a third color and third intensity and upon detecting a change from the user's baseline heart rate, the heart rate rendering changes from the third color and third intensity to a fourth color and a fourth intensity to reflect the change in the user's heart rate.

16. The non-transitory machine-readable storage medium of claim 15, wherein the first orb device is communicatively coupled to the second orb device.

17. The non-transitory machine-readable storage medium of claim 16, wherein the smart phone device, the first orb device, and the second orb device are communicatively coupled to an external medical device.

18. The non-transitory machine-readable storage medium of claim 15, wherein the first and second sets of heartbeat rendering instructions include instructions for the first and second orb devices to employ haptics to create heart rendering effects.

19. A system, comprising:

a computing device equipped with a display and a software application which can generate and send instructions for heart rate rendering;

a first orb device;

a second orb device; and a heart rate monitor, wherein the computing device, the first orb device, the second orb device, and the heart rate monitor are communicatively coupled to each other over a network, wherein the software application on the computing device is configured to determine a user's baseline heart rate, store the user's baseline heart rate, compare the user's present heart rate to the user's baseline heart rate, and generate a first set of heartbeat rendering instructions in response to the comparison; and send the first set of generated heartbeat rendering instructions to a first orb device that is communicatively coupled to the smart phone device to display the user's heartbeat rendering;

wherein the first set of generated heartbeat rendering instructions include instructions to vary light in color and intensity within the first orb device;

wherein when the user's heart rate is at the user's baseline heart rate, the heart rate rendering is a first color and first intensity and upon detecting a change from the user's baseline heart rate, the heart rate rendering changes from the first color and first intensity to a second color and a second intensity to reflect the change in the user's heart rate;

generate a second set of heartbeat rendering instructions in response to the comparison; and send the second set of generated heartbeat rendering instructions to a third orb device that is communicatively coupled to the smart phone device to display the user's heartbeat rendering;

wherein the second set of generated heartbeat rendering instructions include instructions to vary light in color and intensity within the third orb device;

wherein when the user's heart rate is at the user's baseline heart rate, the heart rate rendering is a third color and third intensity and upon detecting a change from the user's baseline heart rate, the heart rate rendering changes from the third color and third intensity to a fourth color and a fourth intensity to reflect the change in the user's heart rate;

generate a third set of heartbeat rendering instructions in response to the comparison; and display heartbeat rendering on the display of the smart phone device in accordance with the generated third set of heartbeat rendering instructions;

wherein when the user's heart rate is at the user's baseline heart rate, the heart rate rendering is a third color and third intensity and upon detecting a change from the user's baseline heart rate, the heart rate rendering changes from the third color and third intensity to a fourth color and a fourth intensity to reflect the change in the user's heart rate.

20. The system of claim 19, wherein the computing device is at least one of a smart phone device, notebook, or personal computer.

* * * * *